(12) United States Patent
Bende et al.

(10) Patent No.: US 6,694,173 B1
(45) Date of Patent: Feb. 17, 2004

(54) NON-CONTACT PHOTOACOUSTIC SPECTROSCOPY FOR PHOTOABLATION CONTROL

(76) Inventors: Thomas Bende, Jahn Strasse #16, Moessinger, D-72116 (DE); Benedikt J. Jean, A.d. Scheibe #30, Sigmarszell, D-88138 (DE)

( * ) Notice: Subject to any disclaimer, the term of this patent is extended or adjusted under 35 U.S.C. 154(b) by 413 days.

(21) Appl. No.: 09/709,133

(22) Filed: Nov. 10, 2000

Related U.S. Application Data
(60) Provisional application No. 60/165,203, filed on Nov. 12, 1999.

(51) Int. Cl.[7] .................................................. A61B 6/00
(52) U.S. Cl. ........................ 600/473; 600/407; 600/443; 600/437; 600/459; 600/463; 600/439; 601/2; 601/3
(58) Field of Search ................................ 600/473, 407, 600/443, 437, 444, 445, 448, 459, 425, 310, 463, 561, 439; 607/57; 128/915, 916; 601/2, 3

(56) References Cited

U.S. PATENT DOCUMENTS

| | | | | |
|---|---|---|---|---|
| 4,378,809 A | * | 4/1983 | Cosman | 600/561 |
| 4,385,634 A | | 5/1983 | Bowen | 128/653 |
| 4,521,118 A | | 6/1985 | Rosencwaig | 374/5 |
| 4,557,607 A | | 12/1985 | Busse | 374/121 |
| 5,036,708 A | | 8/1991 | Urban et al. | 73/801 |
| 5,316,002 A | * | 5/1994 | Jackson et al. | 600/463 |
| 5,657,754 A | | 8/1997 | Rosencwaig | 128/633 |
| 5,713,356 A | * | 2/1998 | Kruger | 600/407 |
| 5,941,821 A | | 8/1999 | Chou | 600/316 |
| 6,070,093 A | * | 5/2000 | Oosta et al. | 600/310 |
| 6,102,857 A | * | 8/2000 | Kruger | 600/437 |
| 6,104,942 A | | 8/2000 | Kruger | 600/407 |
| 6,216,025 B1 | * | 4/2001 | Kruger | 600/407 |
| 6,216,040 B1 | * | 4/2001 | Harrison | 607/57 |
| 6,292,682 B1 | * | 9/2001 | Kruger | 600/407 |
| 6,475,150 B2 | * | 11/2002 | Haddad | 600/448 |
| 6,498,942 B1 | * | 12/2002 | Esenaliev et al. | 600/310 |

* cited by examiner

*Primary Examiner*—Sang Y. Paik
*Assistant Examiner*—Fadi H. Dahbour
(74) *Attorney, Agent, or Firm*—Steven J. Hultquist; Marianne Fuierer

(57) ABSTRACT

A method and system for non-contact laser photoablation to be utilized during vision corrective surgery. Multiple pulses of electromagnetic energy are impinged onto target tissue to ablate and generate an acoustic pressure wave while concurrently processing signals produced by the acoustic pressure wave. A representative pattern can be provided to guide the surgeon through distinct tissue layers encountered in cornea resculpting surgery. Cluster analysis may be utilized to process the acoustic wave signals to generate the representative pattern. Specifically, the representative cluster pattern provides the surgeon with a tool to discern, with increased precision, the tissue layer being ablated and reduces the likelihood of invading a deeper layer of tissue that should not be removed.

34 Claims, 8 Drawing Sheets

NON-CONTACT PHOTOACOUSTIC SPECTROSCOPY FOR PHOTOABLATION CONTROL

CROSS REFERENCE TO RELATED APPLICATION

This application claims the benefit of U.S. Provisional Application Ser. No. 60/165,203 filed Nov. 12, 1999 in the name of Benedikt Jean and Thomas Bende.

BACKGROUND OF THE INVENTION

1. Field of the Invention

The present invention relates generally to laser photoablation, and more specifically to non-contact laser photoablation methods and systems that apply cluster analysis to photoacoustic signals for recognizing tissue compositions during a photoablation procedure.

2. Description of the Related Art

Today, it takes a highly skilled, and specially trained surgeon, with nearly a million U.S. dollars worth of equipment, to perform complicated vision corrective procedures. However, these procedures are only as good as the surgeon's ability to visualize distinctions between different types of corneal tissue. For instance, the doctor must use his own eyesight to see the changes occurring in the patient's tissues occurring during the surgery. Consequently, during a photoablation procedure, while the doctor is removing tissue layers of sub-micron size, it is not possible for the surgeon to visualize the microscopic, delicate changes taking place in the tissue.

A well known form of vision corrective surgery removes a precise amount of tissue from the center of the cornea by utilizing a computer program. The program calculates the precise amount of tissue to be removed by laser vaporization. However, this method does not provide information as to the type of tissue being removed or guidance as to completion of the removal process. As a result, a generic amount of tissue is removed without addressing the specificity of the tissue. Moreover, the uniqueness of each individual is not addressed including the fact that a certain amount of tissue removal in one patient may be beneficial but ineffective and/or detrimental in another patient.

Accordingly, at the present time, a compelling need exists in the art for a photoablation method that discriminates and differentiates between tissues, such as determining corneal epithelium from stroma tissue or healthy tissue from diseased tissue; provides a visual output signal that is representative of the specific tissue being removed; determines the ablation rate; and alerts the surgeon of an approaching interface between tissue to be removed and tissue to be retained, thereby increasing specificity and precision of the photoablation procedure.

SUMMARY OF THE INVENTION

The present invention generally relates to laser photoablation, and more specifically to a method and system for photoablation by impinging multiple pulses of electromagnetic energy onto target tissue to ablate and generate an acoustic pressure wave while concurrently processing signals produced by the acoustic pressure wave. A cluster analysis algorithm may be used to process the generated signals, and as a result, a representative pattern can be provided to guide the surgeon through distinct tissue layers.

The invention, as described hereinafter in greater detail, contemplates in various aspects:

a laser photoablation method that differentiates between distinct tissue layers;

a laser photoablation method and system that together provides a visual signal representative of the specific tissue being removed;

a laser photoablation system that alerts the surgeon of an imminent approach of an interface between removed and retained tissue;

a laser photoablation method that reduces damage to surrounding tissue thereby providing for faster recovering of the patient, increasing success rates of corrective procedures and minimizing risks relating to the surgery; and a laser photoablation method that increases the specificity and precision of a photoablation procedure.

In one specific aspect, the invention relates to a guided non-contact tissue ablation method controllably mediated by recognition of distinct tissue composition within a volume of tissue, the method comprising:

a) impinging multiple pulses of electromagnetic energy onto the tissue to ablate impinged tissue and generate an acoustic pressure wave in response to interaction of the tissue with the electromagnetic energy;

b) non-contactingly sensing the generated acoustic pressure wave and providing a plurality of corresponding signals;

c) processing the signals by applying thereto a cluster analysis algorithm to recognize distinct tissue composition.

The method may further comprise generating a representative pattern of the impinged tissue to recognize distinct layers of tissue composition.

In another aspect, the invention relates to a guided non-contact tissue ablation system that is controllably mediated by recognition of distinct types of tissue composition, the system comprising:

a) at least one electromagnetic energy source for generating multiple pulses of electromagnetic energy to ablate impinged tissue and generate an acoustic pressure wave;

b) at least one non-contacting sensing means for sensing the acoustic pressure wave and providing a plurality of corresponding signals and c) at least one processing means for analyzing the signals of the acoustic pressure wave by a cluster analysis algorithm to recognize distinct tissue composition.

In yet another aspect, the invention relates to a non-contact tissue ablation method controllably mediated by recognition of tissue composition, the method comprising:

a) impinging multiple pulses of electromagnetic energy onto at least one location of the tissue to ablate impinged tissue and to generate at least one acoustic pressure wave in response the electromagnetic energy impinging the tissue;

b) non-contactingly sensing the at least one generated acoustic pressure wave to provide a plurality of corresponding signals; and c) processing the plurality of signals by analyzing a property of the signal to determine change in the ablated tissue.

The signal, formed by the generated acoustic wave, has multiple properties that can be examined and analyzed to provide information concerning location of impingement, change in the ablated tissue type, and changes in the tissue due to interference of acoustic waves. The properties of the emitted signal may include, the frequency, velocity, wavelength, phase of the acoustic wave and the like. If multiple locations are impinged with electromagnetic energy, responses within the tissue, caused by the generated acoustic wave, may be superimposed causing either constructive or destructive interference. This point of interference may be located by implementing triangulation calculations.

Other aspects, features and embodiments of the invention will be more fully apparent from the ensuing disclosure and appended claims.

DETAILED DESCRIPTION OF THE INVENTION AND THE PREFERRED EMBODIMENTS THEREOF

Figure 1:
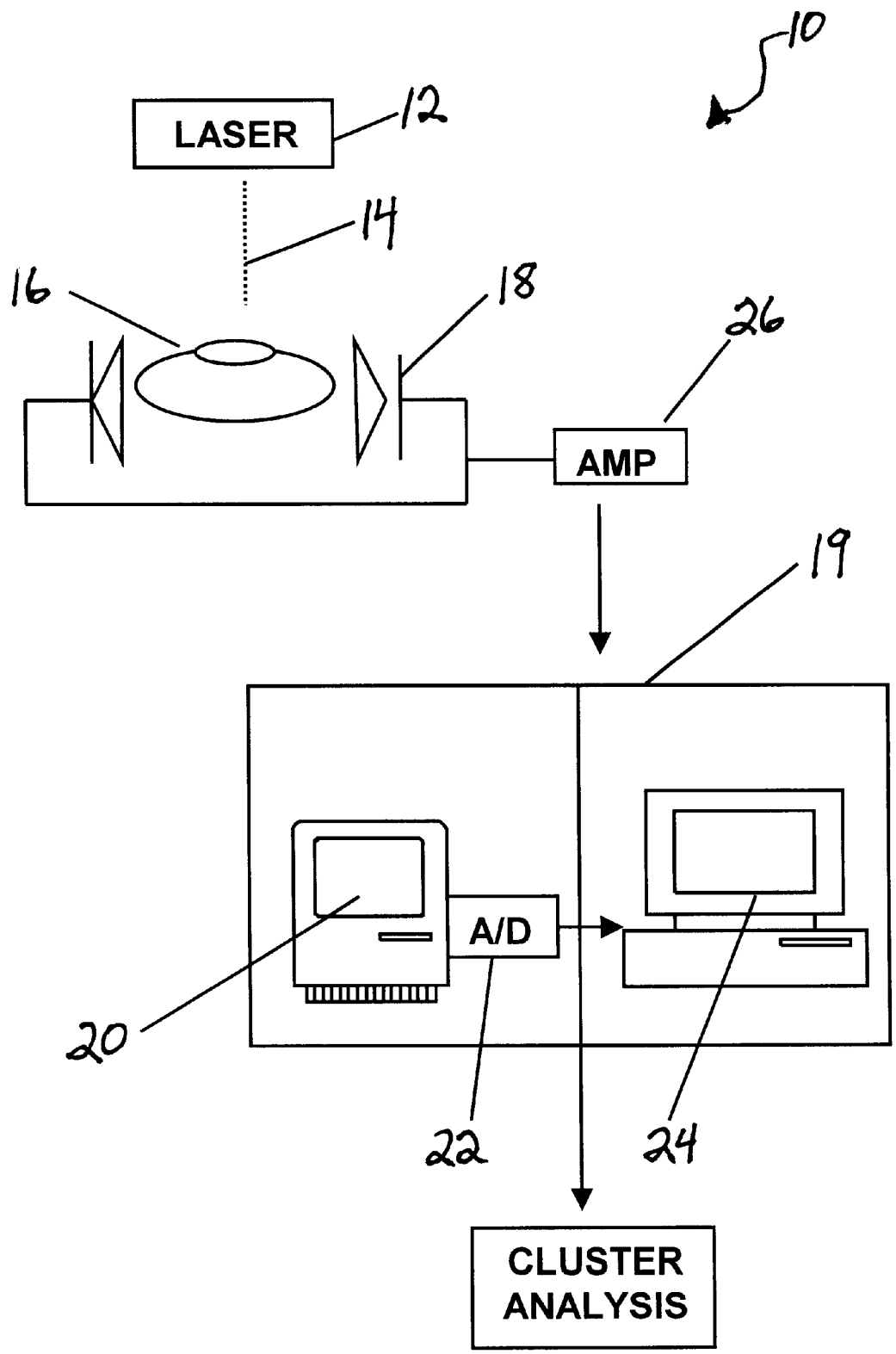
FIG. 1 is a block diagram showing the electronic components of the photoablation system according to one embodiment of the present invention.

The present invention relates to a non-contact laser method and system for vision corrective surgery. It has been discovered that significant benefits are realized in cornea resculpting surgery if an acoustic pressure wave, that emulates from the impinged tissue, is sensed and monitored during the surgery. The acoustic pressure wave is a result of a flash or pulse of laser light impinging on a volume of biological tissue. Absorption of the laser light causes a photoacoustic effect that initiates a host of changes, e.g., electronic rearrangement of the absorbing molecule, vibration energy deposited in surrounding tissue, emission of thermal energy causing expansion of liquid in the tissue, excited molecules emitting light, cleaving of bonds, and the like. All of these changes contribute to an acoustic pressure wave that propagates away from the illuminated region.

Specifically, the acoustic pressure wave has a frequency pattern, unique to each distinct tissue composition, that can be reduced to multiple data points for mathematical manipulation to generate a representative pattern for each layer of tissue during the ablation of the layer. Beneficially, this representative pattern, provides the surgeon with a tool to discern, with increased specificity, exactly which tissue layer is being removed and determine the stratagraphic level of that tissue during the ablation procedure. Moreover, the surgeon can view a monitor or computer screen and determine as different tissue layers are removed and/or when an interface, with an adjacent tissue, is being approached. Fundamentally, the surgeon is equipped with a stratagraphic map definitively showing the current level of ablation and the nearness to another layer of different type tissue. This stratagraphic map increases the surgeon's ability to remove a specific layer of tissue without invading a deeper layer of tissue that should not be removed.

The system can be programmed to alert the surgeon when a different layer of tissue is being approached by an alarm system or color coding of the unique patterns generated by different tissues. An alert system provides the surgeon with increased control during the surgery thereby providing ample time to make adjustments to the lasing system, such as stopping the laser energy, adjusting the laser energy, changing the repetition rate and the like.

Determining the unique properties of an acoustic pressure wave for each tissue layer and mathematically manipulating the data signal output can provide useful data. Determining the speed and velocity of an acoustic wave can provide information on the location of impingement. Determining the frequency of a signal, especially a center frequency peak, provides a mechanism to determine a change in tissue because different types of tissue generate a frequency shift. The frequency shift is the result of interaction of the electromagnetic energy with different types of ablated tissue.

Preferably the data signal output is analyzed through cluster analysis which heretofore has been unknown. Consequently the benefits realized during surgery have not been recognized and/or exploited for the benefit of the patient.

A preferred embodiment of a non-contact photoablation system according to the present invention is described in connection with FIG. 1 which is a block diagram of a typical photoablation device adapted according to the present invention. The non-contact system 10 includes a laser 12 that emits electromagnetic energy in the form of modulated ultraviolet, visible, infrared or microwave radiation 14 that impinges on corneal tissue 16 for absorption and interaction therein.

Generally, any type of laser that produces electromagnetic radiation in the visible, infrared and ultraviolet spectrum may be used in the present invention, including gas, solid-state, organic dye, chemical and excimer lasers. Preferably, the laser generates ultraviolet and infrared radiation in a wavelength band between about 150 nm and about 400 nm, and more preferably, from about 190 nm to about 353 nm. It is known that within this wavelength range, the energy is strongly absorbed by most biological tissue, and thus, a photo-dissociation of the excited molecule occurs without causing necrosis of surrounding tissue.

The photoablation lasers employed in the practice of the invention emit sufficient energy for ablating corneal tissue to modulate the shape of the cornea. The strongest ultraviolet absorption in biological tissue occurs at a wavelength of 193 nm without necrosis of surrounding tissue. As such, the present invention contemplates using lasers that generate an electromagnetic energy beam of photons having wavelengths in the vicinity of 193 nm for the ablation of tissue. However, it is further envisioned that the methods of the present invention are applicable to the use of electromagnetic energy in a wavelength range that does not cause ablation of the tissue, but instead, merely thermal excitation of the tissue.

Regardless of the specific wavelength of the incident radiation employed, the radiation is modulated at a frequency that causes an acoustic pressure wave to be formed. Modulation is accomplished either by using a pulse source, e.g., a pulsed laser (delivering energy in pulses that are less than 0.25 seconds in duration), or a continuous beam laser source with a chopper. The frequency of the modulation should be at a rate that allows the measured photoacoustic signal to oscillate at the same frequency as that of the modulated incident radiation. Generally, modulation frequencies range from about 1 Hz to about 1 kHz, and more preferably from about 5 Hz to about 500 Hz.

The modulation frequency is typically adjusted to a value that is different from any natural environment oscillation that might interfere with the analysis, and more preferably, to a frequency that maximizes the intensity of the signal measured, such as an acoustically resonant frequency. Determining the acoustic resonant frequency and the corresponding appropriate wavelength may be calculated by known methods and equations within the skill of the art.

Excimer lasers, which utilize as the excited medium rare gas halides such as, argon fluoride, krypton fluoride and xenon chloride have been found to be highly effective for use in the present invention. Preferably, an argon fluoride excimer laser is utilized because it produces very precise cuts, as narrow as 20 um, without causing ragged edges at the cutting edge. Especially preferred laser systems include a UV Excimer Laser, type UV 200L, available from Summit Technology, Inc., Waltham, Mass. 02451 and a UV Excimer Laser, type EISIRIS, available from Schwind, Klein-Ostheim, Germany.

It should be noted that the photoacoustic techniques and analysis method and system described herein may be used with any laser system, including those that deliver amplified femtosecond laser pulses that generate microplasmas leading to rapid temperature and pressure increases in the focal spot. The expansion of the hot plasma generates a shock wave that destroys the tissue in the focal spot and this shock wave can also be sensed, measured and analyzed by the methods of the present invention.

In order to target the effect of laser radiation on the tissue of interest and provide the necessary discrimination between different types of tissue, several distinct parameters of the system should be carefully selected. First, the focusing action of the lens can be selected to preferentially supply an irradiance energy of about 80 mJ/cm$^2$ to about 300 mJ/cm$^2$ at the point of impingement of the beam on the tissue. Also, the sensing means should be placed at a distance from the target tissue to allow sufficient signal to reach the sensing means and cause a change therein.

When ablating surface tissue, the laser may be positioned normal to the tissue surface and a single horizontal sweep may be sufficient. However, for a larger area, the laser may be placed in a holder that is attached to a computer system programmed to scan a two dimensional pattern. This may be accomplished by a horizontal sweep and a vertical displacement to place the laser beam in position to complete another horizontal sweep. Providing computerized movement of the laser beam in two directions facilitates multiple pulsing regimes. For instance, the laser beam may ablate tissue at a single localized spot to the desired depth, or in the alternative, the pulsing beam may impinge on a new area of tissue every sequential pulse thereby scanning a larger area of tissue with minimal removal of tissue. This sequential scan may be repeated until the desired depth or removal of tissue is completed.

Additionally, the laser may be placed in a holder in such a way that pivoting of the laser allows for sweeping motion in at least a ninety degree arc in both the x and y direction. Also, the laser may be place on an angle to the surface thereby projecting the energy beam at a predetermined angle.

Another embodiment of the present invention provides for multiple locations of impingement by at least one electromagnetic energy source that deliver energy to the target locations either simultaneously or sequentially. A single laser with a split beam or multiple lasers may be used to impinge on multiple locations. Several points or locations of impingement will generate an interference response within the impinged and surrounding tissue. As discussed above, an interference pattern, formed by superimposing multiple acoustic shock waves, can be used in the ablation process. Constructive interference of the acoustic waves could cause surrounding tissue to be forced into acoustic resonance and/or experience acousto-electric effects, both of which may reduce the requirements of higher intensity energy when ablating surrounding tissue.

The beam profile of the laser may include any known configuration, including circular, rectangular, broad and gaussian shaped beams. Each beam geometric configuration provides unique advantages. For instance, gaussian laser beams, having a higher intensity in the center than at the edges of the beam, are able to penetrate one layer of tissue and show the transition of another layer very early in the ablation process. At the exact moment, the beam penetrates through the first layer a mixed signal is generated that indicates another layer of tissue has been penetrated. This can easily be analyzed because the amplitude of the signal for the first layer will be dampened due to the signal of the next layer of penetration which is visible on a time dependent plot.

A rectangular beam profile, typically emitted by laser diodes, provides uniform irradiance of the tissue at point of impingement. The rectangular beam is able to detect irregularities on the surface of impinged tissue and provides information concerning the different layers being ablated. Rectangular beams are especially useful when smoothening of an irregular surface is required. Specifically, a surface masking material, such as a viscous gel, may be spread on the surface to fill void and provide a layer comprising the masking material and the irregularites of the surface. The ablation process will remove not only the masking material but also the tissue irregularities, thereby providing a mixed signal during the smoothening process. When the irregularities and masking material are removed, a single signal will alert the surgeon that the ablation process is complete.

Broad beam lasers emit a broad beam of electromagnetic energy that is capable of impinging a comparatively large surface area of tissue. Advantageously, this broad coverage of the tissue allows for detecting emitted signals of generated acoustic waves at multiple locations within the tissue.

As stated above, impinging radiation of a sufficient energy will excite tissue molecules during absorption and/or interaction therein. After excitation, some of the molecules within the tissue will return to the ground state by radiationless processes. Shock waves and thermal energy emitted during this relaxation, will cause expansion within the tissue and/or within the surrounding gas, which is usually air. As a consequence of modulating the incident radiation, the tissue or gas will periodically expand and contract. This expansion and contraction can be detected by a sensing means.

Sensing devices 18 are used to capture and detect acoustic signals of the generated pressure waves. Generally, any transducer that converts pressure waves into mechanical energy and/or electrical energy may be used in the present invention. In one preferred embodiment, at least one microphone is used as a transducer that changes a sound wave into an electrical signal. A particularly effective transducer is a capacitor microphone wherein one of the plates is suitably flexible and responds to changing air pressure. Specifically, the changing air pressure, in the acoustic pressure wave, causes one plate of the capacitor C to move back and forth. Because C capacitance is inversely proportional to the separation of the plates, the pressure wave can cause the capacitance to change. This, in turn, causes the charge Q on the plates to change (C=QV) so that an electric current is generated at the same frequencies as the striking pressure wave.

Figure 9:
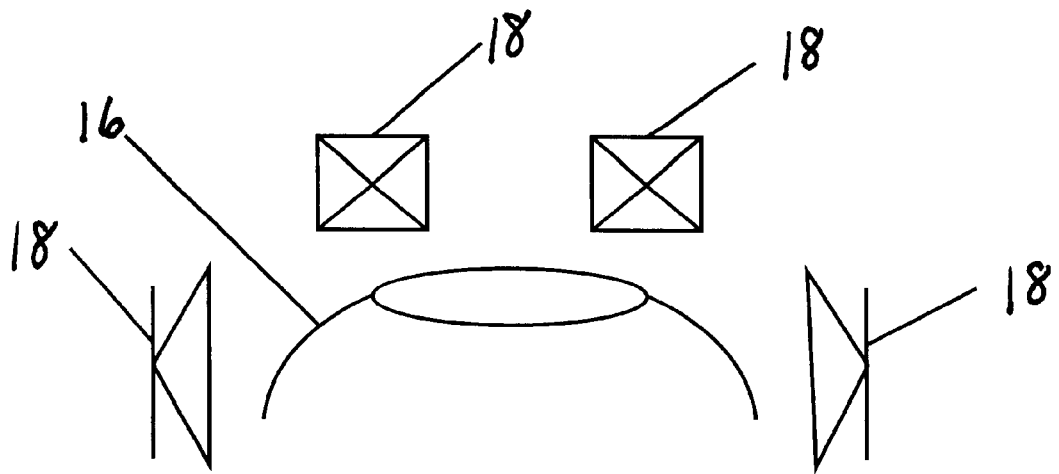
FIG. 9 illustrates a multiple microphone transducer set-up to facilitate the determination of localization of ablated tissue.

In FIG. 1 there is shown two microphone transducers, but it should be recognized that additional microphone transducers may be implemented to provide increased analysis of the impinged tissue, such as shown in FIG. 9. Additional microphones, placed about the impinged tissue, at different locations, to capture signals, can more effectively located a generated response by analyzing the propagation signal from one location and comparing the signal to that captured by other microphones. Analysis may include triangulation calculations, such as those utilized in determining an epicenter of an earthquake. Basically, the speed of an acoustic wave in biological tissue is known or can be determined and the speed of the wave can be used with time measurements. The time measurements may be determined from a time dependent amplitude plot which are generated individually by each of at least three microphones placed at different locations about the tissue, to pinpoint the location of ablated tissue. Additionally, a Fourier analysis of the signals generated by the area of tissue being ablated and measured by a plurality of microphones can be used to locate the source of a noise.

The electric current generated by the microphone transducer, having the same frequencies as the acoustic pressure waves, is sent to a readout device 19. The readout device may include an x-y recorder e.g., video display terminals, plotters and the like. In alternative embodiments, the readout device 19 may include either an oscilloscope 20 or a microprocessor 24 or a combination of both to provide an acoustic signal output representation such as a frequency plot. The acoustic signal output is subsequently mathematically manipulated to generate a representative pattern of a specific layer or tissue type within the cornea. Preferably a cluster analysis algorithm is used to process the signal data.

To increase the electric signal generated by the capacitor microphone, a amplifier 26 may be positioned between the microphone and oscilloscope or computer, to amply the signal output from the sensing microphone. If the laser signal is pulsed, the amplifier will typically be adjusted to respond to the acoustic signal at the pulsed frequency.

Figure 2:
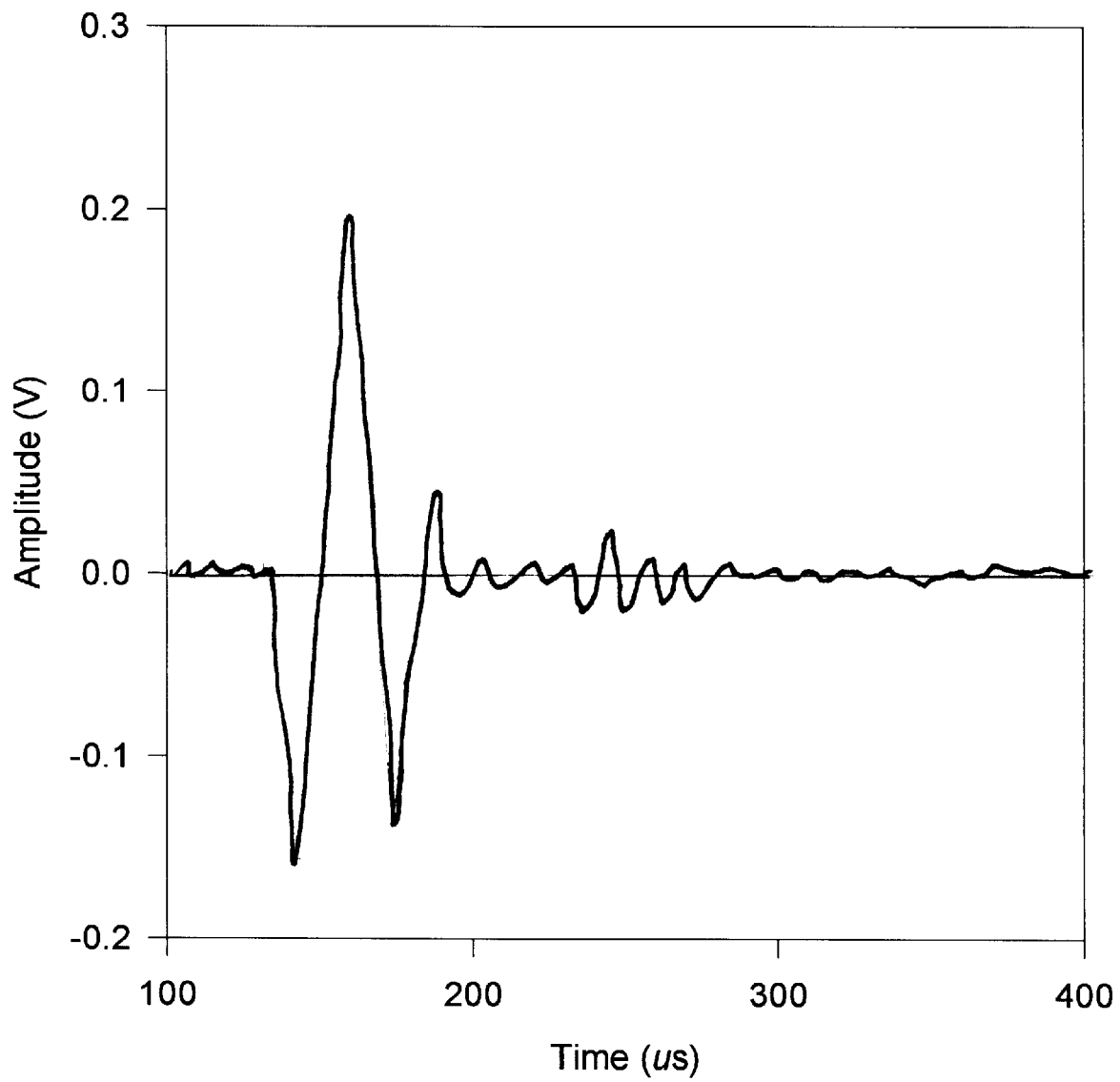
FIG. 2 illustrates an acoustic signal amplitude versus time plot.

The emitted and converted acoustic pressure wave can be displayed on the oscilloscope 20. Any suitable oscilloscope may be utilized in this embodiment to provide a visual output for observing an electrical signal caused by rapidly changing voltages or currents in the acoustic pressure wave. The oscilloscope display may comprise, in visual form, an amplitude (vertical) versus time (horizontal) plot as shown in FIG. 2, wherein the amplitude of the peaks is in response to received signal voltage or current from the microphone. This plot of peaks exhibits the interaction of a pulse of incident radiation with a layer or specific composition of tissue 16.

FIG. 2 provides a visual display of tissue reaction to a pulse of electromagnetic energy. It should be noted that a typical A plot (amplitude of signal v time of arrival at microphone) contains a multitude of information on not only the generated acoustic wave that initially reaches the microphone but also the sound waves that reach the microphone after reflecting from internal tissue surrounding the ablation spot. The electromagnetic energy, impinging the tissue, causes an acoustic wave to travel in all directions including deeper into the unablated tissue. These internal acoustic waves may be reflected by non-homogeneities and discontinuities within the internal tissue, and the microphones will sense the reflected echoes. The location of these captures echoes, for instance on an amplitude versus time plot, provides a visual display of different layers of internal tissue. Each internal layer will cause a reflective acoustic wave to arrive at the sensing mechanism at a different time, dependent upon the depth of interaction. As such, the depth of internal tissue and approaching interfaces between different layers and types of tissue may be monitored to determine their exact location. With this information in hand the surgeon is provided with another tool to increase the specificity of the photoablation process. Fundamentally, the methods of the present invention, not only provide a non-contact method of photoablation, but also, may generate a 3-dimensional image of the internal structure located under the tissue being ablated.

Figure 4:
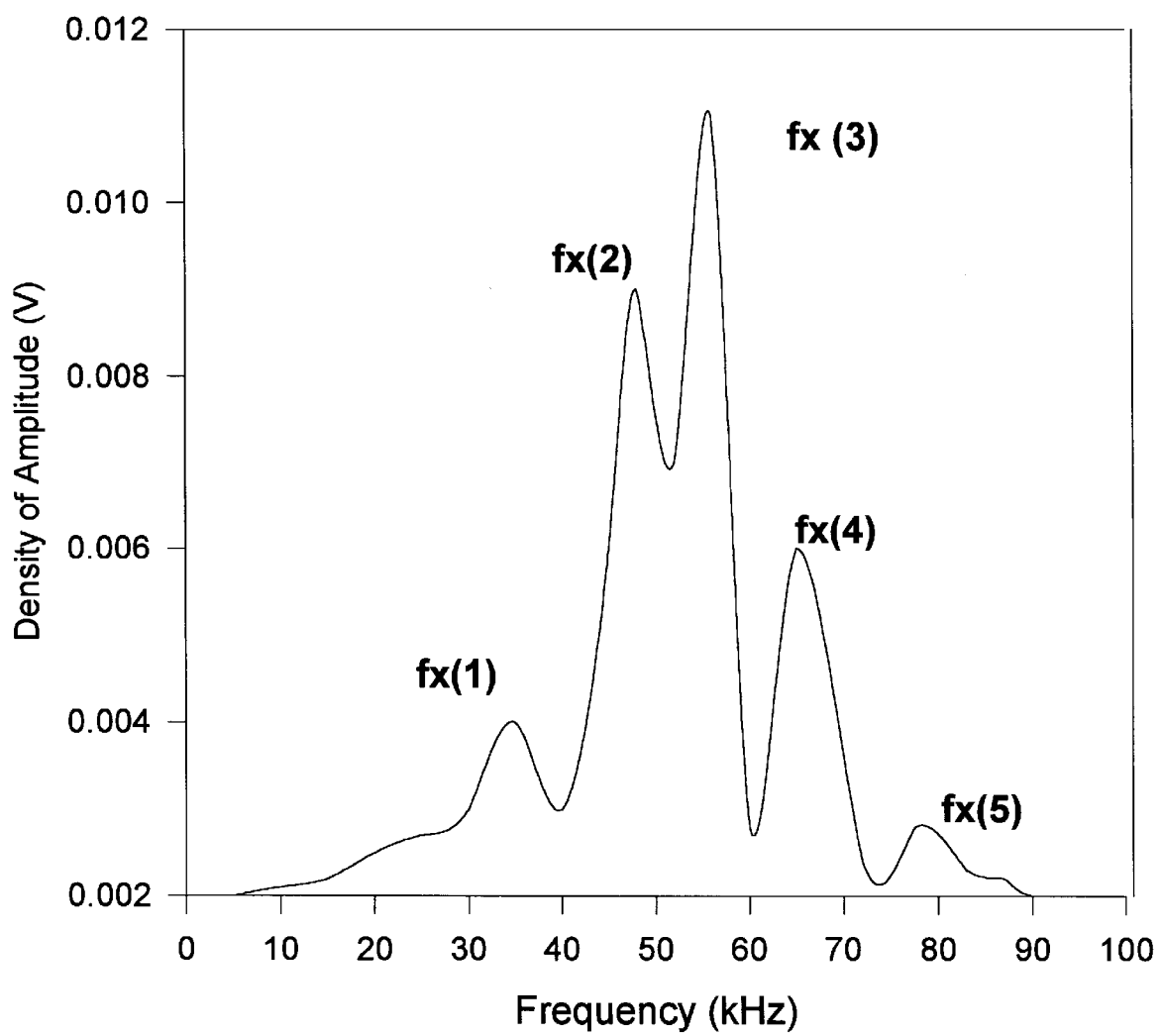
FIG. 4 shows a frequency spectrum of a single pulse photoacoustic signal of PMMA useful for input into a cluster analysis algorithm.

The photoacoustic signals comprising a time domain spectrum (FIG. 2) of the emitted electrical signal provide valuable information relating to the uniqueness of ablated tissue. Preferably, Fourier transformation is used to convert the time domain spectrum to a frequency domain spectrum such as shown in FIG. 4 thereby providing a frequency fingerprint of the absorbing and/or affected tissue containing multiple frequency data points. The center frequency, substantially unique for different types of tissue can be used to indicate a transition from one layer or type of tissue to another layer or type. The center frequency may be calculated by mathematically integrating the frequency depending amplitude over the frequency. Further the frequency shift, that occurs when different tissue are ablated, may be detected by Fourier analysis. Additionally and preferably, sensed multiple frequency data points, typically in the range between 20 Hz and 250 kHz, are mathematically manipulated by cluster analysis to distinguish similar tissues.

Cluster analysis is implemented in order to analyze and classify the photoacoustic frequency data into meaningful groups and to provide a representative cluster pattern for each distinct tissue. Cluster analysis is a method that uses classification algorithms to group objects into clusters. There are a number of different cluster algorithms that may be applicable, e.g., joining, two way joining and K-means clustering.

When the number of classifications is known or hypothesized, such as four classes corresponding to the four layers of tissue in the cornea, which includes the epithelium, Bowman, stroma and endothelium, then applying the k-means clustering algorithm is the most appropriate. In general, the k-means method will produce exactly k different clusters of greatest possible distinction.

There are several variants of the k-means clustering algorithm, but most involve an iterative scheme that operates over a fixed number of clusters, while attempting to satisfy the following properties:
1. Each class has a center which is the mean position of all the samples in that class; and
2. Each sample is in the class having a center that it is closest to.

The basis k-means algorithm consists of the following steps when using a fixed number of classes, such as 4.

1. Initialize: This involves picking a number of pixels (frequency data points) at random from all the data points (for instance, picking 10 out of total of 50), then picking 4 out of the 10 so that the chosen 4 data points have values that are distant from one another. These 4 pixels are used to initialize the 4 classes.
2. All the remaining data points are assigned to a class such that the distance from the data point to the center of the class is minimized. Then the mean of the class is recalculated based on the new data point added to that class. If a data point is no longer in the appropriate class, because the distance to the center is increased, it is moved to another class wherein the distance to the center is decreased. The distance between the data point and center of the class may be determined by using either the Manhattan distance or Euclidean distance equations.
3. Repeat the steps until a termination condition is met which theoretically occurs when data points cease changing classes. However, this may require an unreasonable amount of iterations. Thus an end point, such as 50 iterations may be implemented to provide a reasonable termination point.

The cluster analysis as set forth above can be manually calculated or for a large set of data points a software program may be utilized. A particularly effective software program is commercially available from The MathWorks, Inc., Natick, Mass. 01760, under the trademark MATLAB.

Figure 5:
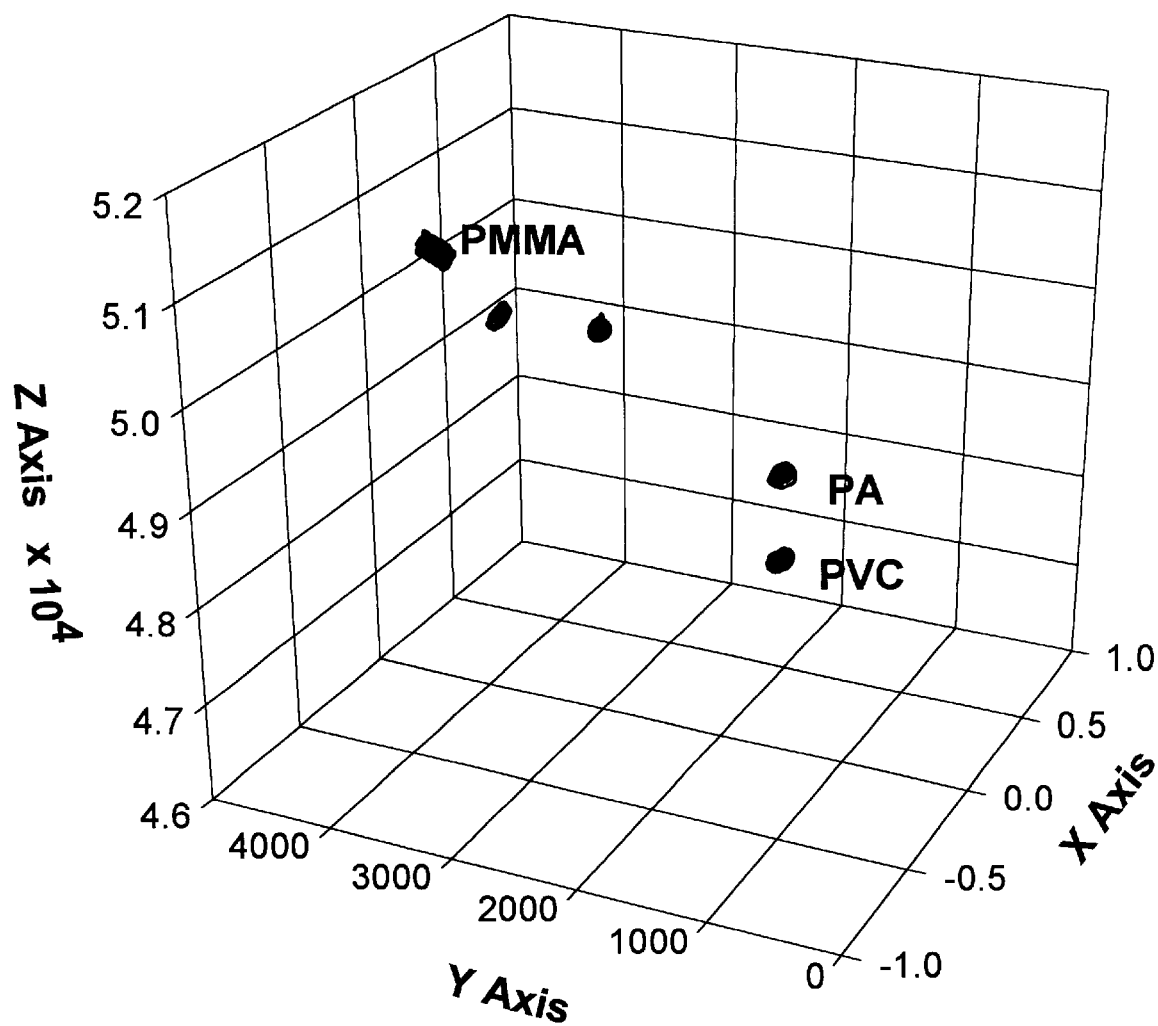
FIG. 5 is a 3-dimensional graph illustrating a representative display showing 3 distinct polymeric compositions.
Figure 7:
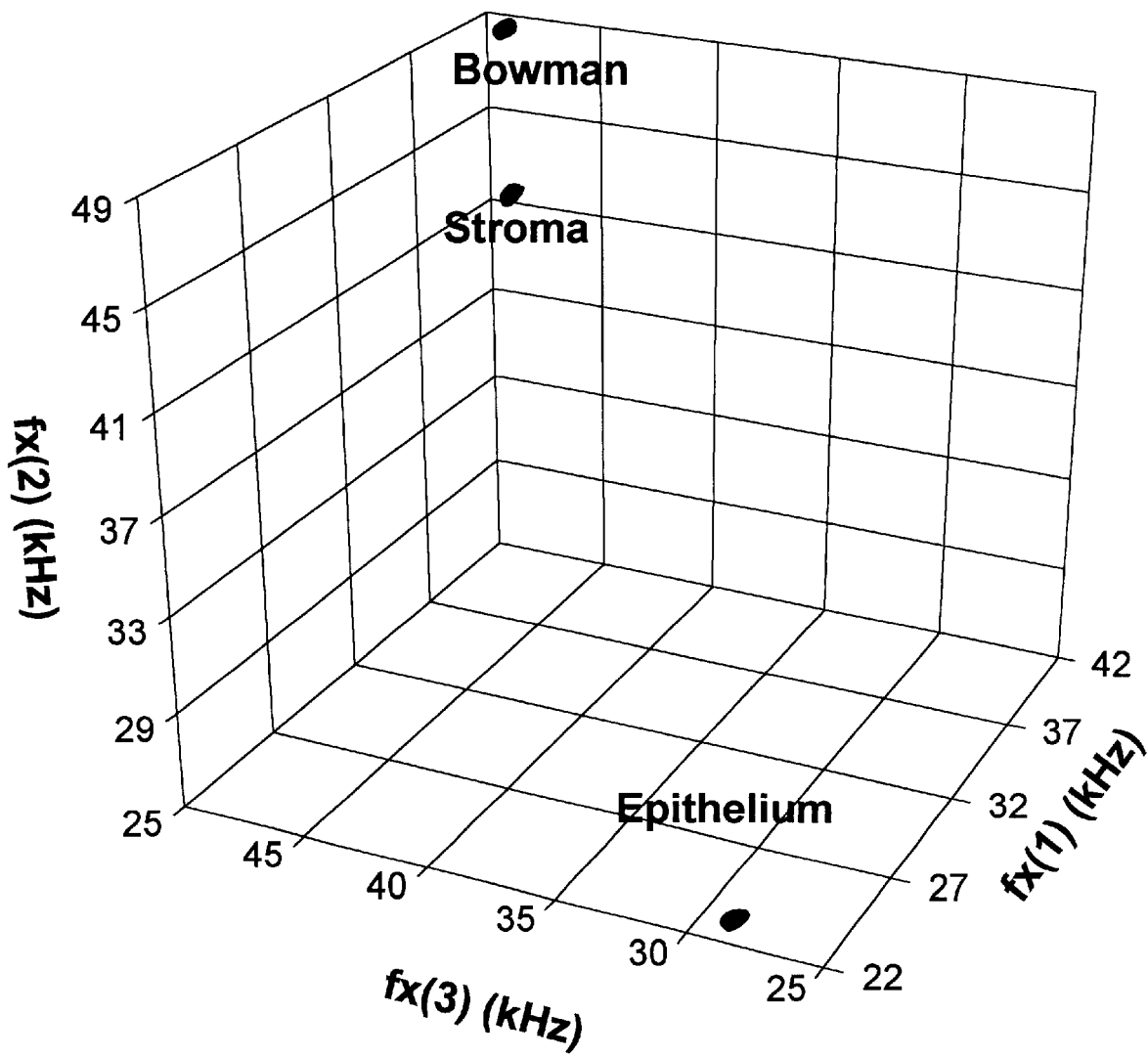
FIG. 7 is a 3-dimensional graph illustrating a representative display showing 3 distinct tissue types and/or layers in normal cornea tissue.

When utilizing a cluster analysis algorithm for classification of materials, different groups of similar material are discernible. For substantially similar materials, local maxima are used for data point input into the cluster algorithm and depending on the number of local maxima it can lead to a multiple clusters groups. As shown in FIG. 5, the application of cluster analysis with the photoacoustic signals generated for the three chemically similar materials, polymethyl-methacrylate (PMMA), polyacrylate (PA), and polyvinylchloride (PVC), yields a visual output that can be displayed on a computer screen to provide recognition of distinct tissue compositions that are easily separable and discernible. FIG. 7 provides a visual output that shows positively that corneal epithelium, Bowman's and stroma tissue can be successfully identified and separated in layers. Advantageously, this visible representation illustrates that separation and discrimination of the three corneal layers is possible, and thus, can limit the amount of tissue removal in typical clinical PRK/TPK procedures with the concomitant effect of limiting the amount of induced iatrogenic hyperopia.

Figure 8:
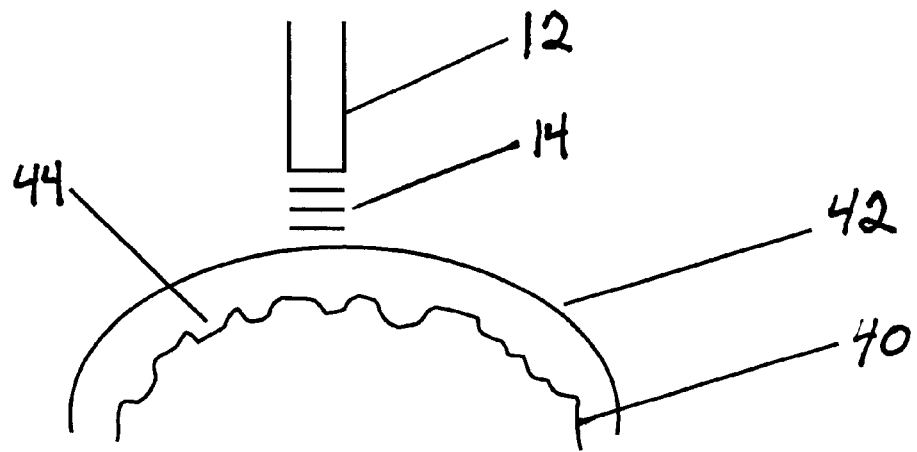
FIG. 8 illustrates a smoothening process with ablation of non-homogeneities in the surface tissue and a surrounding filler material.

FIG. 8 illustrates another aspect of the present invention which provides for a smoothening of a surface having irregularities or non-homogeneities. This is accomplished by covering the surface tissue 40, that is to be ablated, with a material filler layer 42 that fills voids or valleys 44 in the surface tissue thereby forming a film-like mask. To ensure a smooth surface, the film-like mask is ablated along with the surface tissue. Initially, the film and irregularities in the surface tissue will form a mixed signals of acoustic waves generated by the ablated tissue and the material filing the voids. When only a single signal is sensed, the smoothening process is complete. Any filer material may be used that has a similar ablation rate as the surface layer to be ablated. Preferably, the material has gel-like properties, such as water soluble film forming polymers. A list of some representative useful polymers are the water soluble alkyl celluloses, the hydroxyalkyl celluloses, cyclic oligosaccharides ,polydextrose, and the like.

Additionally a fluid may be used as a filler. The fluid is not ablated during the smoothening process, but instead, merely fills voids in the surface to be smoothened. The tissue's water content may be monitored by the photoacoustic signal and the laser's pulse repetition rate may be adjusted, in order to control the water content and/or the amount of water set free, leading to a surface smoothing effect. The fluid may be water that is set free during the ablation process, i.e., cellular water of destroyed body cells or the like. The generated water will fill the voids, but some runoff must be expected during surgery due to the shape of the eye. To compensate for any water lost during the surgery, the pulse rate of the emitted electromagnetic energy source may be increased and/or varied. For example, as water concentration decreases, the pulse rate may be increased to provide additional water. The amount of water can be easily determined by signal analysis, because the measured amplitude of the water signal is determinative of the amount of water set free during the ablation.

The following examples illustrate the various aspects of the present invention for ophthalmic use as a laser ablation method to determine and distinguish similar tissues during an ablation procedure.

EXAMPLE 1

Figure 3:
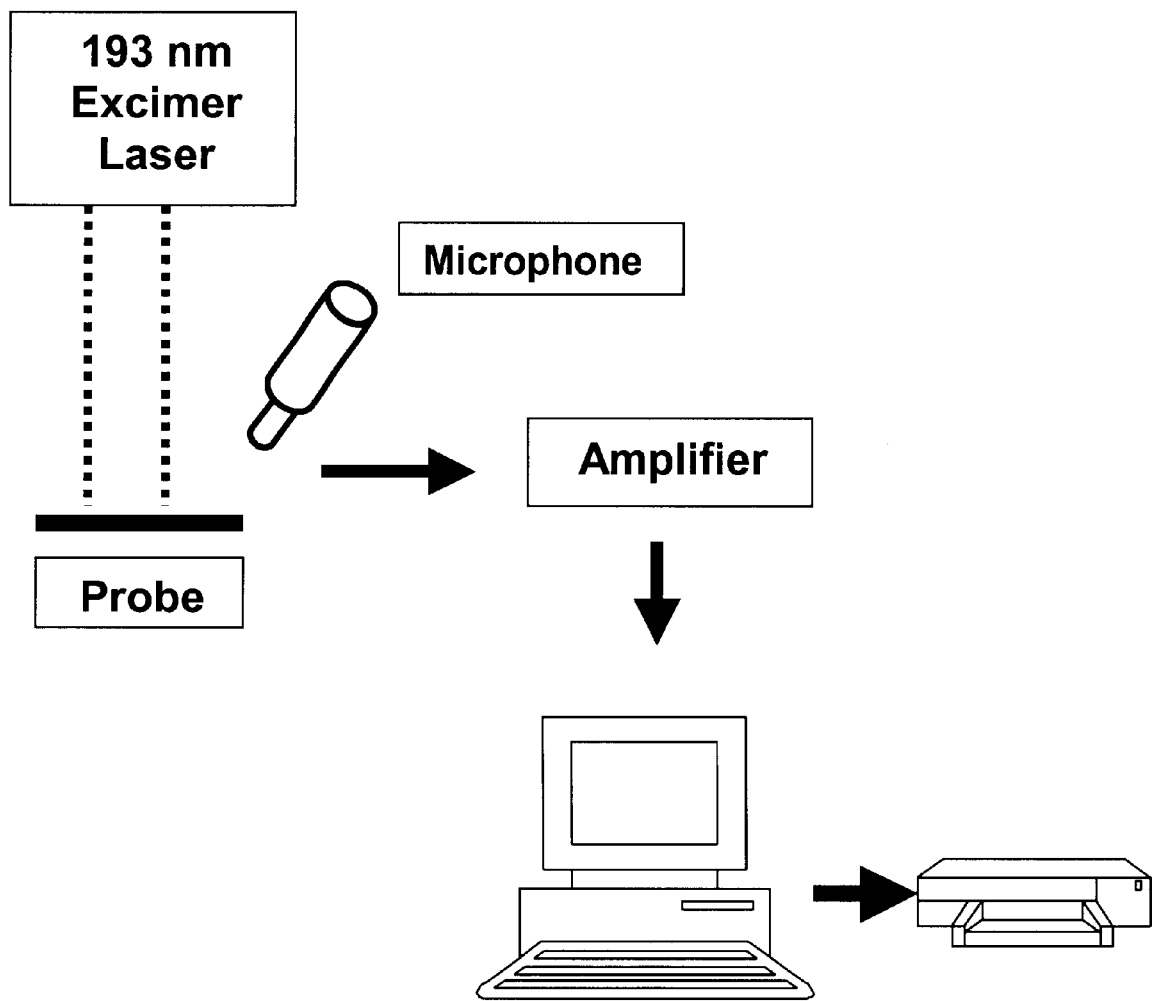
FIG. 3 is an illustrative diagram of an alternative embodiment for impinging tissue with electromagnetic energy according to the present invention.

This example describes a method and system to determine and distinguish similar chemicals according to the present invention. A UV excimer laser (193 nm, from Summit Technology, Inc., type UV 200L) was used for photoablation. The laser parameters were as follows: 10 Hz repetition rate, beam diameters 5.0 mm, fluence 180 mJ/cm$^2$. The fluence was determined by measuring the laser output energy with an external power meter. Organic polymers, polymethyl-meth-acrylate (PMMA), polyacrylate (PA), and polyvinylchloride (PVC) were examined to determine the photoacoustic frequency spectrum for each polymer. Then subsequently the frequency data points were mathematically manipulated through cluster analysis to clearly distinguish the separate polymers. The system configuration and set up, as shown in FIG. 3, included a 193 nm Excimer laser, microphone, amplifier, PC with an A/D converter and printer. The photoacoustic signal was sensed by a capacitor microphone with a frequency range from about 20 Hz to about 200 kHz and an attenuation of 92 dB (Broel & Kjaer, type 2839, preamplifier 2809, microphone power supply 2804). The microphone was positioned 1.0 cm from the target at an angle of 90°. The signal was amplified up to 10 times. The linearly amplified analog signal was analyzed by an A/D converter for further processing to avoid deterioration of the signal quality. A single slot full length 16 bit ISA PC board (CompuScope 2125, GageScope Gage Applied Sciences, Inc., Canada) was used to process the signal output. Two signals were obtained in this manner, the time signal as shown in FIG. 2 and the Fourier transformed signal (frequency spectrum) of FIG. 4. The frequency spectrum from the Fourier transform signal was investigated by inputting frequency data points into a cluster analysis algorithm (k-means). Specifically, the center maximum frequency and the four (4) closest local frequency maxima were selected, that being f(x) 1, 2, 3, 4, and 5 as shown in FIG. 4. The converted data was analyzed with the MatLab™ language program (MatLab 5.2, from The Mathworks, Inc.). The frequency spectrums for PMMA, PA and PVC were analyzed by cluster analysis and the results transferred to a 3-dimensional cluster plot as shown in FIG. 5. Results: Implementing cluster analysis provides for a visual output illustrating the separate polymers. The center frequency, fx (3) in FIG. 4, was used to initialize the cluster analysis for PMMA and the remaining frequency maxima were grouped according to the distance to the central frequency. (It should be noted that PMMA is composed of several points and each point represents a variation of laser parameters, e.g., fluence, beam diameter.) Frequency signals from the other polymers were entered and analyzed accordingly. In this manner, very similar polymers were distinguished. Moreover, it is shown that variations of laser parameters in the same target material results in insignificantly small shifts within a cluster cloud for the same target material, and the cluster is easily separable from chemically similar materials.

EXAMPLE 2

Figure 6:
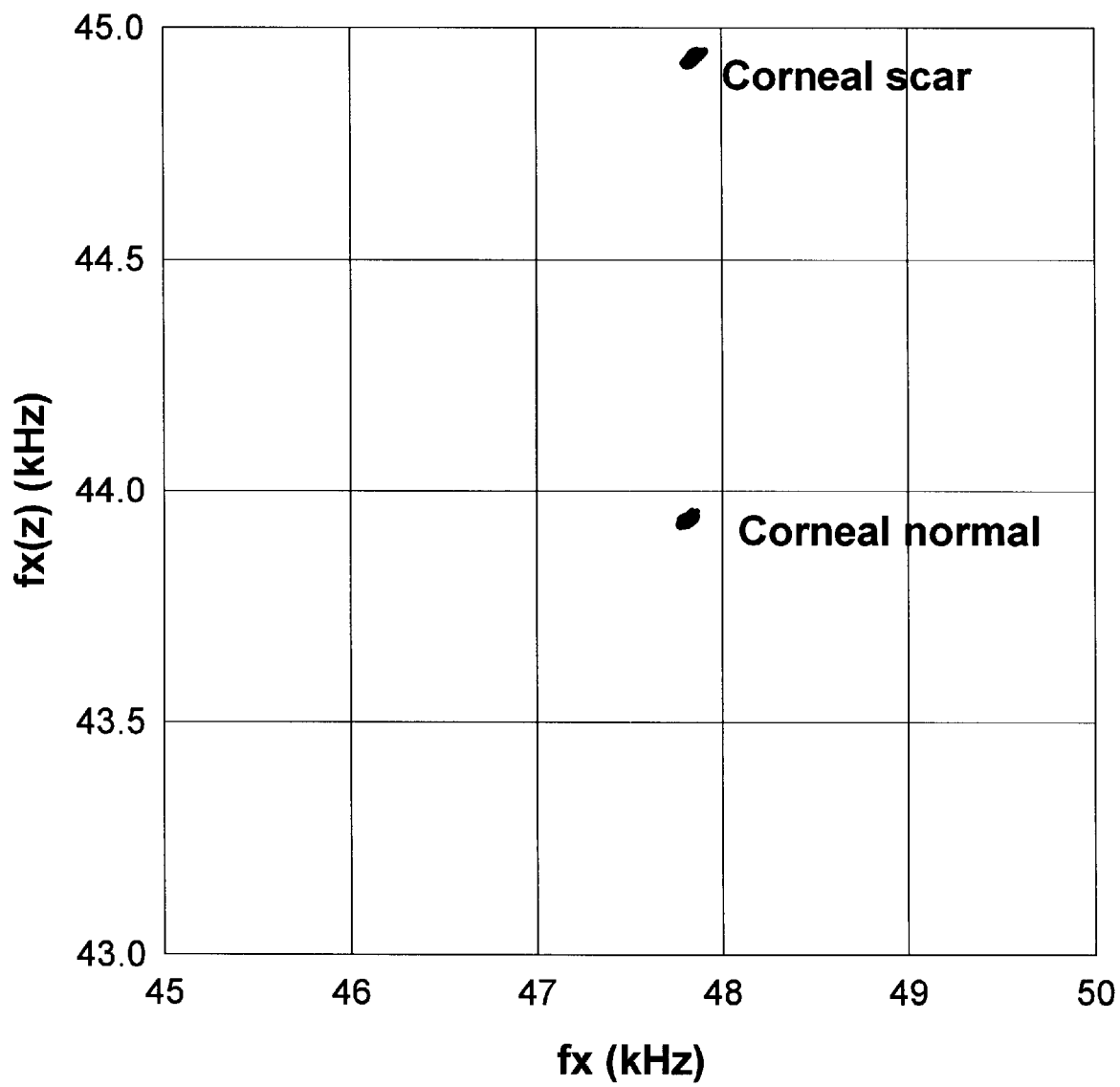
FIG. 6 is a 2-dimensional graph illustrating a representative display recognizing the difference between normal and scarred cornea tissue.

This Example describes determining and distinguishing normal porcine cornea tissue from scar porcine cornea tissue. To discriminate normal corneal tissue from corneal scar tissue, the photoacoustic signal for two freshly removed porcine corneas were compared to corneas with photothermally induced scar tissue. Stromal coagulation was induced by contact application with a LTK laser by meandering the contact band piece in an area measuring 7 by 7 mm. The same laser, sensing and computer set-up used in Example 1 was used herein except that the laser beam diameter was increased to 6.0 mm and the microphone was placed 16 cm from the tissue at an angle of 20°. Cluster analysis was performed on the frequency spectrums and the results are shown in FIG. 6.

Results: For essentially different tissue, such as corneal scar tissue and normal cornea tissue, a 2-dimensional cluster plot suffices for reproducible discrimination. Such 2-dimensional cluster analysis reduces the time and complexity of signal processing and thus provides an easily identified representation of different materials that can easily transfer to an operating room environment.

EXAMPLE 3

This example describes determining and distinguishing the different layers of cornea tissue including corneal epithelium, Bowman's layer and stroma during an in vivo and in situ photoablation (PRK) procedure. The same laser, sensing and computer set-up used in Example 1 was used during the surgery except that the laser beam diameter was increased to 6.0 mm and the microphone was placed 16 cm from the tissue at an angle of 20°. Cluster analysis was performed on the data of the frequency spectrums generated during the ablation process with the results shown in FIG. 7.

Results: The successful identification and separation of the corneal layers has been demonstrated by using the non-contact photoacoustic methods of the present invention in a typical clinical PRK/TRK procedure. The three corneal layers are easily discernible, in contrast to the use of a surgical microscope, and as such, the method of the present invention provides for recognition of a transition interface between scar tissue and normal stroma tissue. Thus, the methods of the present invention could minimize unnecessary tissue removal and consequently limit the amount of induced iatrogenic hyperopia.

The ablation methods of the present invention may be used for any surface. Especially, it may be used for restoration of paintings or other historically important surfaces. Further, it may be used to clean metallic surfaces, like steel to remove oxidations layers, such as rust.

While the invention has been described herein with reference to specific features, aspects and embodiments, it will be recognized that the invention may be widely varied, and that numerous other variations, modifications and other embodiments will readily suggest themselves to those of ordinary skill in the art. Accordingly, the ensuing claims are to be broadly construed, as encompassing all such other variations, modifications and other embodiments, within their spirit and scope.

That which is claimed is:

1. A guided non-contact tissue ablation method controllably mediated by recognition of distinct tissue composition within a tissue volume, the method comprising:
    a) impinging multiple pulses of electromagnetic energy onto the tissue to ablate impinged tissue and generate an acoustic pressure wave in response to the electromagnetic energy interacting with the impinged tissue;
    b) non-contactingly sensing the generated acoustic pressure wave to provide a plurality of corresponding signals;
    c) processing the plurality of signals by applying thereto a cluster analysis algorithm to recognize distinct tissue composition.

2. The guided non-contact tissue ablation method of claim 1 further comprising generating a representative pattern of the impinged tissue illustrating distinct tissue layers.

3. The guided non-contact tissue ablation method of claim 1 wherein the plurality of signals is an acoustic signal sensed from the acoustic pressure wave.

4. The guided non-contact tissue ablation method of claim 3 wherein the acoustic signal is Fourier transformed and a maximum peak is chosen as a center frequency and at least four closest frequency maxima are chosen to be processed in the cluster analysis algorithm.

5. The guided non-contact tissue ablation method of claim 1 wherein the electromagnetic energy has a wavelength in a range of from about 150 nm to about 400 nm.

6. The guided non-contact tissue ablation method of claim 1 wherein the electromagnetic energy is emitted by a laser.

7. The guided non-contact tissue ablation method of claim 6 wherein the laser is an excimer laser generating the electromagnetic energy with a wavelength of 193 nm.

8. The guided non-contact tissue ablation method of claim 1 wherein the generated acoustic pressure wave is non-contactingly sensed by a transducer.

9. The guided non-contact tissue ablation method of claim 8 wherein the transducer comprises is a capacitor microphone.

10. The guided non-contact tissue ablation method of claim 1 wherein the generated acoustic pressure wave is generated by the absorption of the electromagnetic energy by the impinged tissue.

11. The guided non-contact tissue ablation method of claim 1 wherein the cluster analysis comprises performing a k-means algorithm.

12. A non-contact tissue ablation method controllably mediated by recognition of tissue composition, the method comprising:
    a) impinging multiple pulses of electromagnetic energy onto at least one location of the tissue to ablate impinged tissue and to generate at least one acoustic pressure wave in response to the electromagnetic energy impinging the tissue;
    b) non-contactingly sensing the at least one generated acoustic pressure wave to provide a plurality of corresponding photoacoustic signals; and
    c) processing the plurality of photoacoustic signals by analyzing frequencies that are characteristic to specific types of tissue to determine change in the ablated tissue.

13. The guided non-contact tissue ablation method of claim 12 further comprising generating a representative pattern of the impinged tissue illustrating distinct tissue layers.

14. The guided non-contact tissue ablation method of claim 12 wherein the change in the ablated tissue is determined upon observation of a frequency shift from a first frequency that is characteristic to said tissue before ablation to a second frequency that is characteristic to said tissue after ablation.

15. The guided non-contact tissue ablation method of claim 12 wherein the electromagnetic energy has a wavelength from about 150 nm to about 400 nm.

16. The guided non-contact tissue ablation method of claim 15 wherein the electromagnetic energy is emitted by a laser.

17. The guided non-contact tissue ablation method of claim 16 wherein the laser comprises an excimer laser generating the electromagnetic energy having a wavelength of 193 nm.

18. The guided non-contact tissue ablation method of claim 12 wherein the generated acoustic pressure wave is non-contactingly sensed by at least one microphone transducer.

19. The guided non-contact tissue ablation method of claim 12 wherein the electromagnetic energy is emitted by a laser have a beam configuration selected from the group consisting of gaussian, rectangular, circular, point beam and broad beam.

20. The guided non-contact tissue ablation method of claim 19 wherein the beam comprises a broad beam to impinge electromagnetic energy onto an area of tissue and signals formed by the generated acoustic wave are sensed at multiple locations of the impinged tissue.

21. The guided non-contact tissue ablation method of claim 19 further comprising applying a material filer to the tissue before impinging area with the laser, the laser having the rectangular beam configuration to ablate impinged tissue and material filler.

22. The guided non-contact tissue ablation method of claim 12 wherein the signal property to be analyzed is frequency.

23. A guided non-contact tissue ablation method controllably mediated by recognition of tissue composition, the method comprising:
   a) impinging multiple pulses of electromagnetic energy into at least one location of the tissue to ablate impinged tissue and to generate at least one acoustic pressure wave in response to the electromagnetic energy impinging the tissue;
   b) non-contactingly sensing the at least one generated acoustic pressure wave to provide a plurality of photoacoustic signals; and
   c) processing the plurality of photoacoustic signals by Fourier transformation, to choose a maximum as a center frequency and at least four closest frequency maxima;
   d) analyzing the central frequency and the four closest frequency maxima to determine change in the ablated tissue, using a cluster analysis algorithm.

24. A guided non-contact tissue ablation method controllably mediated by recognition of tissue composition, the method comprising:
   a) impinging multiple pulses of electromagnetic energy onto at least one location of the tissue to ablate impinged tissue and to generate at least one acoustic pressure wave in response to the electromagnetic energy impinging the tissue;
   b) non-contactingly sensing the at least one generated acoustic pressure wave to provide a plurality of corresponding signals; and
   c) processing the plurality of signals by performing cluster analysis using a k-means algorithm to determine change in the ablated tissue.

25. A guided non-contact tissue ablation method controllably mediated by recognition of tissue composition, the method comprising:
   a) impinging at least two pulses of electromagnetic energy from at least two electromagnetic energy sources onto at least two locations on the tissue to ablate impinged tissue and to generate multiple acoustic waves that superimposed to provide an interference response;
   b) non-contactingly sensing the multiple generated acoustic pressure waves and the interference response to provide a plurality of corresponding signals; and
   c) processing the plurality of signals by analyzing at least one signal property to determine change in the ablated tissue.

26. The guided non-contact tissue ablation method of claim 25 wherein the pulses are emitted simultaneously or sequentially.

27. The A guided non-contact tissue ablation method controllably mediated by recognition of tissue composition, the method comprising:
   a) impinging multiple pulses of electromagnetic energy onto at least one location of the tissue to ablate impinged tissue and to generate at least one acoustic pressure wave in response to the electromagnetic energy impinging the tissue;
   b) non-contactingly sensing the at least one generated acoustic pressure wave to provide a plurality of corresponding signals.
   c) processing the plurality of signals by analyzing at least one signal property to determine change in the ablated tissue; and
   d) adjusting impinging electromagnetic energy according to fluid content of tissue.

28. A guided non-contact tissue ablation system that is controllably mediated by recognition of distinct types of tissue composition, the system comprising:
   a) at least one electromagnetic energy emitting source to generate multiple pulses of electromagnetic energy to ablate impinged tissue and generate an acoustic pressure wave in response to the electromagnetic energy impinging the tissue;
   b) at least one non-contacting sensing means for sensing the acoustic pressure wave and providing a plurality of corresponding photoacoustic signals; and
   c) at least one processing means for analyzing the photoacoustic signals of the acoustic pressure wave to determine frequencies that are characteristic to specific types of tissue and to recognize distinct tissue composition based on said characteristic frequencies.

29. The guided non-contact tissue ablation system of claim 28 further comprising a display means for displaying a representative pattern of the impinged tissue illustrating distinct tissue layers.

30. The guided non-contact tissue ablation system of claim 29 wherein the at least one non-contacting sensing means comprises a microphone transducer.

31. The guided non-contact tissue ablation system of claim 28 wherein the at least one electromagnetic energy source comprises a laser.

32. The guided non-contact tissue ablation system of claim 31 wherein the processing means comprises an oscilloscope operatively coupled with a computer.

33. A guided non-contact tissue ablation system that is controllably mediated by recognition of distinct types of tissue composition, the system comprising:
   a) at least one electromagnetic energy emitting source to generate multiple pulses of electromagnetic energy to ablate impinged tissue and generate an acoustic pressure wave in response to the electromagnetic energy impinging the tissue;
   b) at least one non-contacting sensing means for sensing the generated acoustic pressure wave and providing a plurality of corresponding signals; and
   c) at least one processing means for analyzing the signals of the acoustic pressure wave using a cluster analysis algorithm to recognize distinct tissue composition.

34. The guided non-contact tissue ablation system of claim 33 wherein the at least one electromagnetic energy source comprises an excimer laser generating the electromagnetic energy having a wavelength of 193 nm.

* * * * *